United States Patent [19]

Kolpak

[11] Patent Number: 5,224,372
[45] Date of Patent: Jul. 6, 1993

[54] MULTI-PHASE FLUID FLOW MEASUREMENT

[75] Inventor: Miroslav M. Kolpak, Plano, Tex.

[73] Assignee: Atlantic Richfield Company, Los Angeles, Calif.

[21] Appl. No.: 781,434

[22] Filed: Oct. 23, 1991

Related U.S. Application Data

[63] Continuation-in-part of Ser. No. 523,152, May 14, 1990, Pat. No. 5,090,253.

[51] Int. Cl.⁵ ............................................. G01N 33/00
[52] U.S. Cl. ................................... 73/19.03; 73/19.10
[58] Field of Search ............ 73/861.04, 861.37, 861.38, 73/19.01, 19.03, 19.05

[56] References Cited

U.S. PATENT DOCUMENTS

| | | | |
|---|---|---|---|
| 3,927,565 | 12/1975 | Pavlin et al. | 73/861.38 X |
| 4,096,745 | 6/1978 | Riukin et al. | 73/861.37 X |
| 5,029,482 | 7/1991 | Liu et al. | 73/861.04 X |

*Primary Examiner*—Herbert Goldstein
*Attorney, Agent, or Firm*—Michael E. Martin

[57] ABSTRACT

Multiphase (gas and two liquid phases) fluid flowstreams are measured to determine the total flow rate, fluid density, the fraction of gas, and one liquid in the total liquid mixture by passing the flowstream through a Ceriolis flow meter (16, 40), a densimeter (12) and a meter (14) which measures the fraction of one liquid in the two liquid mixture. The total fluid flow rate may be measured by a single tube flow meter (40) having adjacent loops which provide tube legs (49, 51) positioned adjacent each other and vibrated laterally at a predetermined frequency and amplitude while measuring pressures in the contraflowing streams in the adjacent tube legs. The density and gas fraction of the flowstream may be determined by vibrating a tube containing the flowstream over a range of frequencies and measuring the phase angle and amplitude of the fluctuating fluid pressures compared with acceleration of the tube to determine the sloshing natural frequency of the fluid mixture. The tube may be vibrated at a frequency far from the sloshing natural frequency of the fluid mixture to determine the fluid density.

12 Claims, 2 Drawing Sheets

MULTI-PHASE FLUID FLOW MEASUREMENT

CROSS REFERENCE TO RELATED APPLICATION

This application is a continuation in part of application Ser. No. 07/523,152, filed May 14, 1990, now U.S. Pat. No. 5,090,253, the subject matter of which is incorporated herein by reference.

BACKGROUND OF THE INVENTION

1. Field of the Invention

The present invention pertains to methods and apparatus for measuring multi-phase fluid flow such as mixtures of oil, water and gas utilizing a densimeter, a two-phase flow meter based on microwave attenuation characteristics and a mass or volumetric flow meter such as a modified coriolis-type flow meter.

2. Background of the Invention

Various techniques and systems have been developed for measuring multi-phase fluid flow, in particular, three phase fluid flow comprising a mixture of oil, water and gas. My U.S. Pat. No. 4,852,395, assigned to the assignee of the present invention describes a system for measuring multiphase fluid flow wherein gas is separated from a mixture of oil and water and the fractions of oil and water are then determined including measuring batch samples to correct for the residual gas content. Although such a system has a high degree of accuracy, it is relatively mechanically complex and requires a gas separator and gas flow meter.

Mechanically simple flow meters are sought for many applications, particularly in applications for measuring the multiphase fluid emanating from oil and gas wells wherein essentially, mixtures of water, hydrocarbon liquids, such as crude oil; and gas are continually produced in varying proportions of the total fluid flowstream. The present invention provides new and unique methods for measuring multiphase fluid flow, particularly of the type above described, as well as improved apparatus for measuring such multiphase fluid flow, which overcomes some of the problems associated with prior art methods and systems.

SUMMARY OF THE INVENTION

The present invention provides improved methods for measuring multiphase fluid flow, such as mixtures of oil, water and gas.

In accordance with one aspect of the present invention a method is provided for measuring the oil, water and gas flow rates of a multiphase fluid flowstream without completely separating any of the fluid fractions from the flowstream. A system for practicing the method includes a meter which measures the oil and water fractions of the flowstream, a densimeter and a coriolis type flow meter. The oil-water fraction or "watercut" meter may be one of several types but is preferably one based on microwave attenuation characteristics which vary with the fraction of oil and water, respectively. The coriolis type flow meter may be of the type described in co-pending U.S. patent application Ser. No. 07/523,152.

In another system and method according to the invention, the fractional volumetric flow rates may be determined using only, in combination, the watercut meter and the modified coriolis type flow meter.

The present invention still further provides unique methods and apparatus for determining the gas fraction and density of a multiphase fluid mixture utilizing a single continuous tube type device which is vibrated substantially at the sloshing resonant frequency of the fluid mixture, or determining the density of a fluid mixture by vibrating the device at a frequency substantially away from the sloshing resonant frequency. Still further, there is provided a method and system utilizing a single continuous tube type flow meter with tube portions wherein the fluid flow at a predetermined point is in opposite directions and wherein the difference in fluid pressures at selected locations in the tube are measured to determine mass flow rate.

Those skilled in the art will recognize the above-described advantages and superior features of the present invention together with other important aspects thereof upon reading the detailed description which follows in conjunction with the drawing.

DESCRIPTION OF PREFERRED EMBODIMENTS

Figure 1:
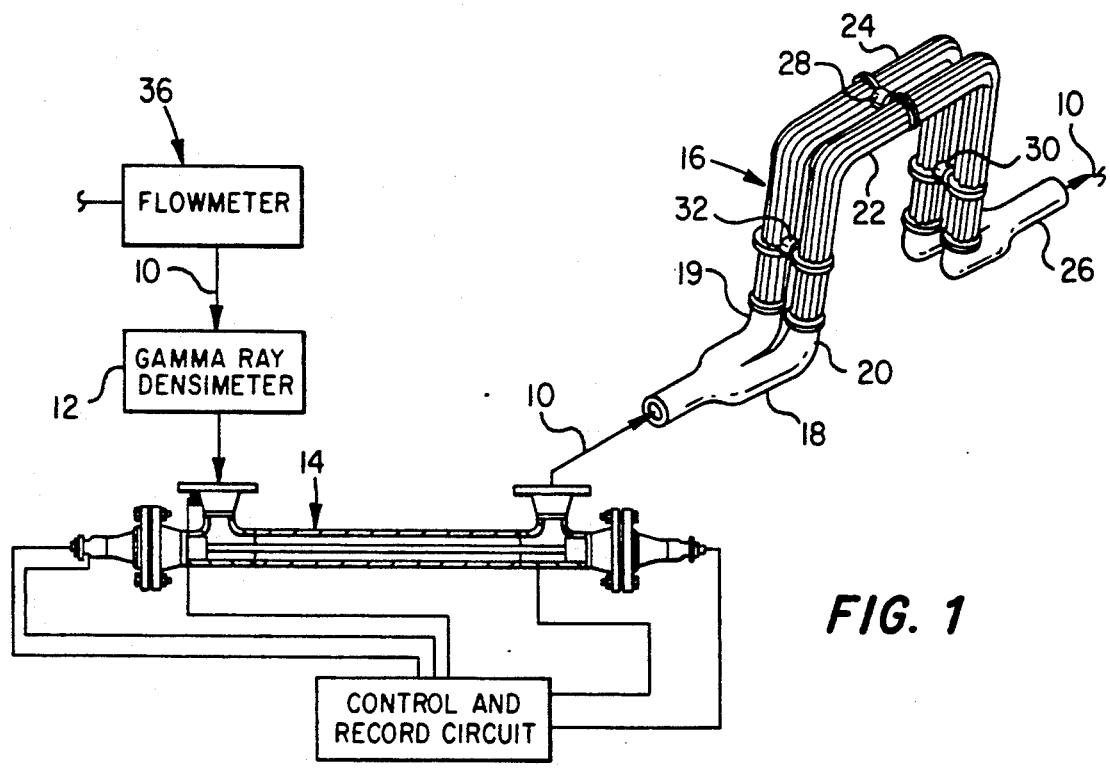
FIG. 1 is a schematic diagram illustrating one combination of measurement devices used in conjunction with the methods of the present invention.
Figure 2:
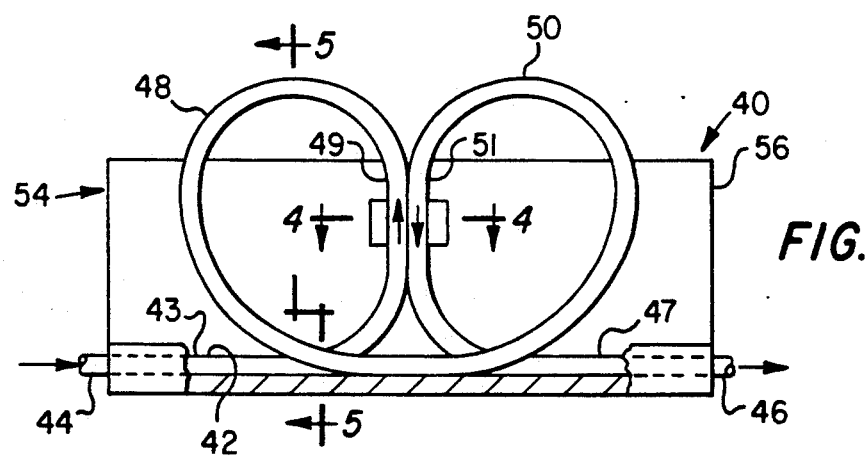
FIG. 2 is a side elevation of a single continuous tube type flow measuring apparatus in accordance with the present invention.
Figure 3:
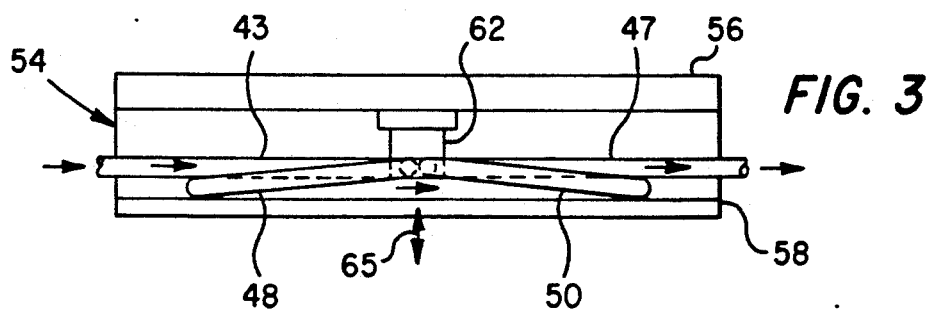
FIG. 3 is a top plan view of the apparatus shown in FIG. 2.

In the description which follows like parts are marked throughout the specification and drawing with the same reference numerals, respectively. The drawing figures are not to scale and certain features are shown in schematic form in the interest of clarity and conciseness. Referring to FIG. 1, there is illustrated a conduit 10 which is operable to conduct a multiphase fluid flowstream, such as might result from the production of crude oil from a well, and which typically includes a mixture of crude oil, water and gas. The systems and methods described herein are more accurate when the gas content of the fluid flowstream is less than about twenty percent (20%) of the total. Preliminary separation of gas might be necessary in some situations in order to prepare the flowstream for measurements by the system of the present invention. In FIG. 1, four separate devices are shown interposed in the conduit 10 and which devices may be used in certain combinations or alone to make certain measurements in accordance with the present invention. A densimeter 12 is interposed in the conduit 10 which may be of the so-called gamma ray type, for example. The densimeter 12 may be of a type commercially available, such as a model S-Series "Sensor Net" manufactured by TN Technologies, Inc. of Round Rock, Tex. A second device shown interposed in the conduit 10 for receiving flow of fluid therethrough is a so-called "watercut" meter, generally designated by the numeral 14, and of the type which measures changes in microwave attenuation resulting from changes in the composition of the fluid flowing therethrough. The meter 14 is preferably of the type disclosed and claimed in U.S. Pat. Nos. 4,862,060 issued Aug. 29, 1989 or 4,996,490 issued Feb. 26, 1991 both to Scott et al. and both assigned to the assignee of the present invention. Suffice it to say that the meter 14 is operable to measure the water fraction of an oil-water mixture which may include certain amounts of gas entrained therein.

FIG. 1 further illustrates a modified coriolis type flow meter, generally designated by the numeral 16, which may be of the type described in application Ser. No. 07/523,152. Basically, the flow meter 16 comprises an inlet conduit 18 which is split into two branch conduits 19 and 20 which are in communication with respective bundles of smaller diameter tubes 22 and 24, having a generally U-shaped configuration, and connected to an outlet manifold 26 similar to the manifold or conduit 18. The tube bundles 22 and 24 are vibrated in a generally lateral direction with respect to their longitudinal central axes by suitable vibrator means 28 and the vibrations of the respective upstream and downstream legs of the tube bundles 22 and 24 are sensed by vibration sensors 30 and 32. Further details of the flow meter 16 may be obtained by referring to the above-referenced patent application.

In accordance with a first method the gas, water and oil flow rates in a multi-phase fluid flowstream flowing through the conduit 10 may be determined utilizing the densimeter 12, a meter such as the meter 14, and the coriolis flow meter 16, for example. The densimeter 12 provides measurement of the total fluid mixture density, dm, and the coriolis flow meter 16 provides measurement of the apparent mixture density, dma, which is related to the true mixture density, dm, by the equation:

$$dm = dma(1 + A2 \cdot fg + A3 \cdot fg^2) \quad (1)$$

where A2 and A3 are coefficients which may be determined earlier by calibration of the meter 16 in gassy liquid flow wherein small uniformly distributed gas bubbles are present in the range of zero percent (0%) to twenty percent (20%) by volume in the liquid, and fg is the gas fraction of the multi-phase fluid flowstream. Equation (1) may be solved for the gas fraction, fg, which then takes the form:

$$fg = \frac{\sqrt{A2^2 - 4A3(1 - dm/dma)}}{2A3} \quad (2)$$

The coriolis type flow meter 16, is operable to provide a measurement of the apparent mass flow rate of the fluid flowstream, Ma, which is related to the true mass flow rate, M, by the equation:

$$M = Ma(1 + A4 \cdot fg + A5 \cdot fg^2 + \ldots) \quad (3)$$

where A4, A5, ... are coefficients which are also determined earlier by calibration of the coriolis meter 16 in gassy liquid flow wherein small uniformly distributed gas bubbles are present in the range of zero percent (0%) to twenty percent (20%) by volume, in the liquid.

The oil, water and gas volumetric flow rates Qo, Qw, and Qg are computed by:

$$Qo = Qm(1 - fg)(1 - wc) \quad (4)$$

$$Qw = Qm(1 - fg) \cdot wc \quad (5)$$

$$Qg = Qm \cdot fg \quad (6)$$

where Qm is the volumetric flow rate of the fluid mixture determined by:

$$Qm = M/dm \quad (7)$$

where dm and M are computed by equations (1) and (3) substituting the value of the gas fraction, fg, determined in equation (2) and the value of the water fraction, wc, as determined by the meter 14. The method just described above provides volumetric flow rates for the oil fraction, the water fraction and the gas fraction without the need of knowing the density of each of these components.

On the other hand, in situations where the water density, the oil density and the gas density are known or are easily measured and are relatively stable from time to time over the period where flow measurement is desired, the flow rates of each of the fractions of gas, water and oil in the multi-phase flowstream may be determined by a second method using a watercut meter and a modified coriolis type meter such as the meters 14 and 16, respectively. The coriolis meter 16 will provide a measurement of the apparent density of the mixture, dma, which may be used to determine the true density, dm, from equation (1). The gas fraction, fg, is related to the density values and the water fraction (on a volumetric basis) by the following equation:

$$fg = [wc(dw - do) + (do - dm)]/[wc(dw - do) + (do - dg)] \quad (8)$$

where fg is the gas fraction, wc is the water fraction measured by the meter 14, do is the oil density, dw is the water density and dg is the gas density.

Simultaneous solution of equations (1) and (8) yields $$fg = \frac{\sqrt{b^2 - 4ac}}{2a}$$

where $$a = dma \cdot A3 \quad (9)$$

$$b = dma \cdot A2 + wc(dw - do) + (do - dg) \quad (10)$$

$$c = dma - wc(dw - do) - do \quad (11)$$

wc = measured by meter 14 dma = measured by coriolis meter 16 do,dw,dg = known (measured) densities of oil, water and gas

The oil, water and gas flow rates Qo, Qw, and Qg may then be computed using equations (4) through (6). Accordingly, a method utilizing only two meters, namely the meters 14 and 16 may be used if the densities of the fluid fractions can be measured and remain relatively constant. Inaccuracies caused by imprecise knowledge of the oil density and the water density when oil gravity is low (API gravity approaches about 10) do not occur.

In accordance with a third method of the present invention, the flow rates of the fractional fluid components of a multi-phase fluid flowstream flowing through the conduit 10 may be determined utilizing a watercut meter such as the meter 14, a flow meter such as the modified coriolis meter 16 or a flow meter 36 and an apparatus such as the type described in FIGS. 2 through 5.

Referring now to FIGS. 2 through 5 there is illustrated an apparatus for use in measuring the flow rate of a multiphase fluid stream including a mixture of gas and liquid. The apparatus illustrated is generally designated by the numeral 40 and is characterized by a continuous double loop of tubing or conduit 42 having an inlet end 44 and a discharge end 46. The conduit 42 includes two vertically disposed loops 48 and 50 positioned adjacent to each other such that one portion or "leg" 49 of the loop 48 is directly adjacent one leg 51 of the loop 50. The conduit 42 is supported on a mounting plate 54 having an upstanding wall 56, and a base portion 58 with a slot 60, FIG. 5, formed therein for supporting the conduit 42, as illustrated. A suitable vibrator device 62 is mounted on the wall 56 and is engaged with the legs 49 and 51 of the respective tube loops 48 and 50 for vibrating the legs 49 and 51 laterally with respect to their central longitudinal axes.

Figure 4:
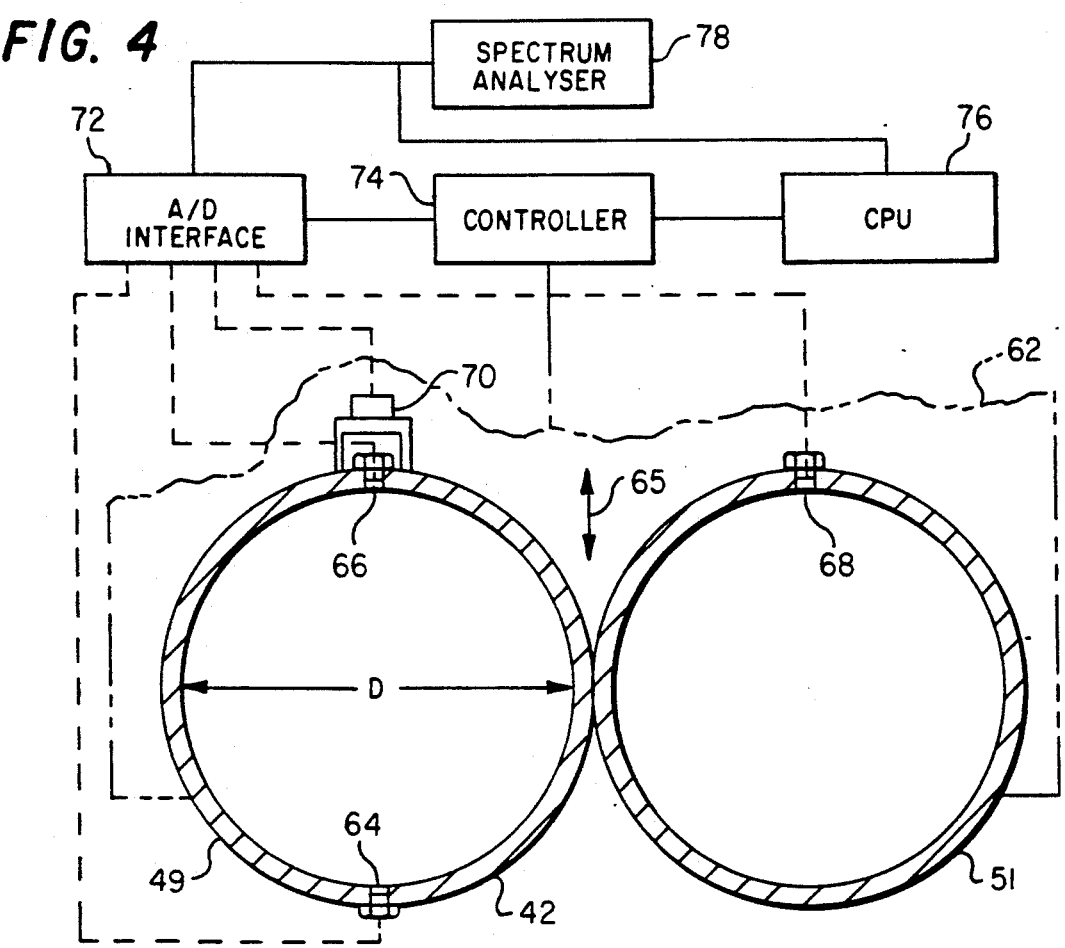
FIG. 4 is a section view taken along the line 4—4 of FIG. 2 illustrating an arrangement which is used in conjunction with a method of the present invention.
Figure 5:
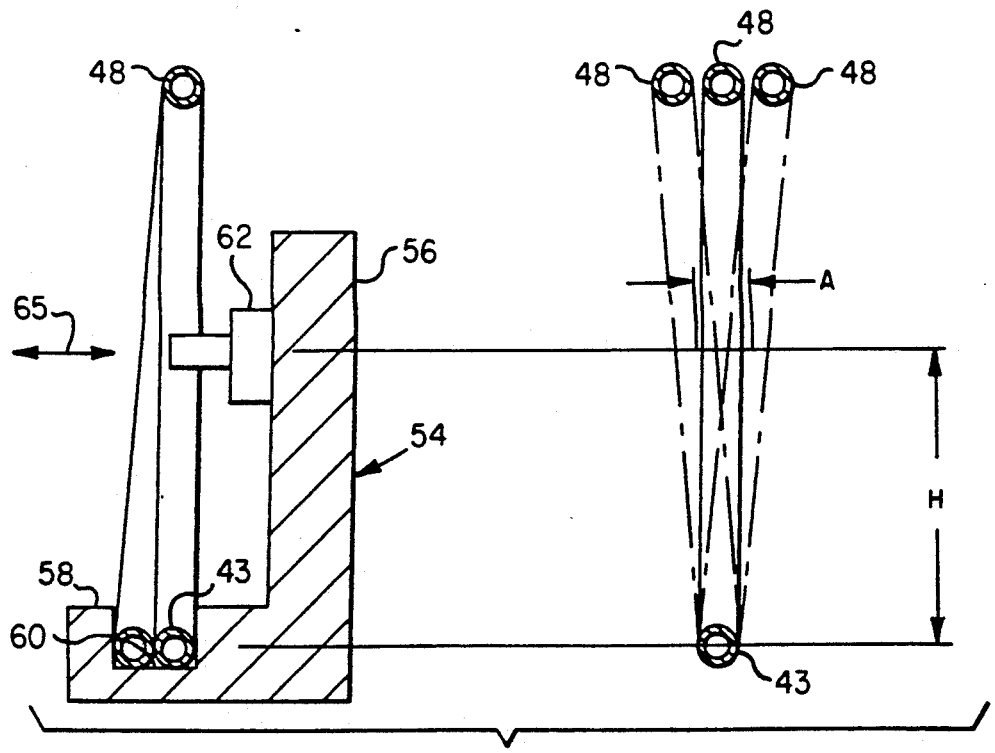
FIG. 5 is a section view taken along line 5—5 of FIG. 2 and including a diagram illustrating some of the dimensions used in accordance with the method of the present invention.

As shown in FIG. 4, suitable pressure transducers 64 and 66 are mounted on the tube leg 49 opposed to each other and aligned with the direction of vibration or oscillatory movement of the tubing legs 49 and 51, as indicated by the arrows 65. A third pressure transducer 68 is mounted on the tubing leg 51, as indicated in FIG. 4, for measuring pressures within the leg. FIG. 5 illustrates also how the loops 48 and 50, including their respective legs 49 and 51, oscillate about a pivot point formed by the portions of the tube 42 which lie in the slot 60. For example, the loop 48 generally pivots about the central longitudinal axis of the leg 43, FIG. 2, and the loop 50, in like manner, pivots about the longitudinal central axis of the leg 47, both of which lie coaxially with respect to each other in the slot 60.

The apparatus 40 may be used in determining the volumetric and mass flow rates of a multiphase fluid stream in place of the flow meter 16. For example, the volumetric flow rate ($Q_m$) of the fluid flow stream maybe determined from the equation:

$$Q_m = A_c[\{(P_{66} - P_{68}) - dPf\}/\{19.7 \times D \times dm \times H \cdot x(A/H)\}] \quad (12)$$

where $A_c$ is the cross sectional area of the conduit 42 at the measurement point, $P_{66}$ and $P_{68}$ are the pressures measured at the transducers 66 and 68 at the instant of peak lateral acceleration of the legs 49 and 51, respectively, D is the tube inner diameter, dm is the density of the fluid mixture in the tube, which may be determined by one of the aforementioned methods, A is the amplitude of vibration of the loops 48 and 50, Hz is the frequency of vibration of loops 48 and 50, H is the distance indicated in FIG. 5 between the pivot point of vibration of the loops 48 and 50 and the point of measurement of the pressures $P_{66}$ and $P_{68}$ and dPf is the friction pressure drop between the transducers 66 and 68 which is an average value of the difference in the pressures $P_{66}$ and $P_{68}$ over a period of time greater than about ten oscillations of the loops 48 and 50.

Typical order of magnitude values of the difference between the peak pressures $P_{66}$ and $P_{68}$ are indicated below for a tube or conduit having a nominal diameter of 2.0 inches and a fluid mixture flowing therethrough having a density of 2.0 slugs and a ratio of vibration amplitude (A) to (H) of 1:50. It will be seen that for a vibratory frequency of 80 Hz and for the fluid velocities (v) indicated below, that the required sensitivity of the transducers 66 and 68 will be as indicated by the last column which is the derivative of pressure with respect to time.

| v ft/sec. | $P_{66}-P_{68}$-dPf (psi) | $d(P_{66}-P_{68})/dt$ (psi/sec.) |
|---|---|---|
| 2 | .073 | 36 |
| 20 | .730 | 360 |

Again, in cases where the water density, oil density and gas density are known and are relatively stable from time to time, the apparatus 40 may also be used to determine the gas fraction, fg, of the mixture flowing through the conduit 10 utilizing the meter 14, the flow meter 36 or 16 and the apparatus 40.

Referring further to FIG. 4, the apparatus 40 may also include a transducer or accelerometer 70 mounted on the conduit leg 49 in such a way as to measure accelerations of the leg 49 in the directions of the arrows 65. The transducers 64, 66, 68 and 70 may be connected to a suitable control system including an analog to digital interface 72, a controller 74, a computer or "CPU" 76 and a frequency spectrum analyzer 78. The volumetric or mass flow rate of a fluid mixture flowing through the apparatus 40 may also be determined by measuring the gas fraction mixture (fg) using the apparatus 40 instead of other methods. The measurement may be carried out by vibrating the conduit leg 49 in the direction of the arrows 65 at the natural frequency of vibration (fn) of the liquid mixture flowing through the leg 49. Assume that the natural frequency of vibration (fn) of the fluid mixture flowing through the leg 49 has a generally sinusoidal waveform and a phase lag, as measured by the transducer 64 or 66, of approximately 90 degrees with respect to the waveform of the vibration of the conduit leg 49 as measured by the transducer 70. The vibrator 62 may be controlled to sweep through a range of frequencies while measuring the phase angle of vibration of the fluid mixture as determined by the transducer 66 as compared with the waveform of the vibration of the leg 49 as determined by the transducer 70. When this phase angle is 90 degrees, as determined by the spectrum analyzer 78, the "sloshing" natural frequency (fn) of the compressible mixture of fluid in the leg 49 may be noted and the following equation solved for the gas fraction, fg:

$$fg = \frac{\frac{1}{dm(4Dfn)^2} - b}{1/P - b} \quad (13)$$

where dm is the density of the fluid mixture, D is the inside diameter of the conduit leg 49, b is the bulk compressibility of the liquid in the fluid mixture, which can be assumed, and P is the nominal fluid pressure in the conduit leg 49. In the limit, as the gas fraction, fg, approaches 0 or 1, the natural frequency of vibration of the fluid mixture will become that corresponding to the quarter wave resonance of a sonic wave in the conduit leg 49, that is, the medium being all liquid (fg=0) and all gas (fg=1), respectively. Predicted values of fn for a 1.0 inch, 2.0 inch, and 3.0 inch diameter pipe, assuming that the density of liquid is 60 lb./ft.$^3$, the bulk compressibility of the liquid is $3.5 \times 10^{-6}$ in.$^2$/lb. and the nominal pressure is 500 psig, indicate the natural sloshing frequency of the fluid mixture will be in a range of sound detectable by the human ear.

An advantage of the arrangement illustrated in FIG. 4 and the method described above, is that, in high pressure applications, conventional coriolis flow meters require that the pipe or conduit be so stiff that a signal to noise ratio is too small for accurate measurements. The apparatus 40 may be operated to determine the density (dm) of the fluid mixture if the gas fraction (fg) is known and equation (13) is solved for dm.

The oil, water and gas flow rates Qo, Qw, and Qg are each computed by equations (4) through (6) in which Qm is the volumetric flow rate determined from the flow meters 36 or 16. The meter 16 need not be used in the method just described but the fluid densities do, dw, dg and the bulk compressibility, b, as well as the pressure, P, must be known.

Alternatively, the apparatus may be operated to effect vibration of the conduit leg 49 at a frequency far from the "sloshing" natural frequency of the fluid mixture flowing through the conduit 42. Under these circumstances lateral acceleration in the direction of the arrows 65 will match those of the vibrating conduit leg 49. Accordingly, by sweeping the frequency of vibration induced by the vibrator 62 through a range and noting the accelerations measure by the transducers 64, 66 and 70, while also simultaneously measuring the pressure at the points of measurement determined by the transducers 64 and 66, will yield an oscillating pressure whose amplitude is related to fluid density by the equation:

$$dm = (g)(P1-P2)/(D^*A(2\pi Hz)^2) \quad (14)$$

where g is the gravitational constant, P1 and P2 are the pressures measured at the respective opposed transducers 64 and 66, D is the inside diameter of the conduit leg 49, A is the amplitude of vibration of the conduit leg 49 and Hz is the frequency of vibration of the conduit leg.

The oil, water and gas flow rates can thus be computed by equations (4) through (6). The flow meter 36 or 16 may be used to determine Qm.

Conventional coriolis meters determine the fluid mixture density (dm) by measuring the natural frequency of the "pipe-fluid" combination. This arrangement has worked well when structural stiffness of the pipe is not high, such as would be required in relatively high pressure applications as mentioned above. However, the pipe stiffness does not affect the determination of the fluid mixture density (dm) in the methods described above. Other advantages of these methods are that the noise to signal problems such as those which are inherent in conventional coriolis meters are absent, entrained gas bubbles should not adversely affect the density measurement, as long as the vibration frequency is far from the natural sloshing frequency and only one tube or conduit need be used to obtain the fluid mixture density data, thereby minimizing pressure drops across the flowmeter. Moreover, precise dimensions and dynamic balancing of the conduit is not required, such as is the case with conventional coriolis type flow meters.

Volumetric and mass flow rates may thus be determined for a mixed phase fluid from a relatively simple single tube flow meter wherein the coriolis effects are measured more directly than with conventional coriolis flow meters. Instead of measuring the distortion and resonance of vibrating tubes, the actual pressures of the fluids flowing through the tubes are measured and related to density and volumetric or mass flow rate.

Although preferred embodiments of the present invention have been described in detail herein, those skilled in the art will recognize that various substitutions and modifications may be made to the specific embodiments described without departing from the scope and spirit of the invention recited in the appended claims.

What is claimed is:

1. A method of determining the gas fraction of a multiphase fluid flowstream comprising gas, and at least two liquids in the liquid phase comprising the steps of:

providing means for measuring the true density of the fluid flowstream and a Coriolis device for determining the apparent density of the fluid flowstream;

flowing the fluid flowstream through said means and said device thereby measuring the true and apparent densities of the fluid; and determining the gas fraction based on the true density of the fluid flowstream and the apparent density of the fluid flowstream.

2. The method set forth in claim 1 including the step of:

measuring the mass flow rate of the fluid flowstream with the coriolis device; and determining the volumetric flow rate of the fluid flowstream based on the mass flow rate and the density of the fluid flowstream.

3. The method set forth in claim 2 including the steps of:

providing means for measuring the liquid fraction of at least one of the two liquids in the fluid flowstream;

measuring the liquid fraction of said at least one liquid;

determining at least one of the volumetric flow rate of the liquid phases and the gas phase in the fluid flowstream based on the volumetric flow rate of the fluid flowstream, the gas fraction, and the liquid fraction of said at least one liquid.

4. The method set forth in claim 1, wherein: said Coriolis device comprises at least one tube through which the fluid flowstream is conveyed, said tube is vibrated in a lateral direction with respect to the direction of flow of fluid through said coriolis device and the gas fraction (fg) is determined by the relationship:

$$fg = \frac{\sqrt{A2^2 - 4A3(1 - dm/dma)}}{2A3}$$

wherein dma is the apparent density of the mixture as determined by the Coriolis device, dm is the true density of the fluid mixture and A2 and A3 are empirical coefficients obtained by calibrating said coriolis device with gassy liquid flow.

5. A method of determining the gas fraction of a multiphase fluid flowstream comprising gas, and at least two liquids in the liquid phase wherein the density of the gas and the liquids is known, comprising the steps of:

providing a Coriolis device for measuring the apparent density of the fluid flowstream and a meter for determining the fraction of one liquid in the liquid phase of the fluid flowstream;

flowing the fluid flowstream through said meter and said device thereby measuring the apparent density and fraction of one liquid; and determining the gas fraction based on the measured apparent density of the fluid flowstream, the known densities of the gas and the liquids and the measured fraction of one liquid in the liquid phase.

6. The method set forth in claim 5 including the steps of:

measuring the mass flow rate of the fluid flowstream with the Coriolis device; and determining the volumetric flow rate of the fluid flowstream based on the measured mass flow rate and the density of the fluid flowstream.

7. The method set forth in claim 6 including the steps of:

determining the volumetric flow rate of at least one of the liquid phases and the gas phase in the fluid flowstream based on the volumetric flow rate of the fluid flowstream, the gas fraction, and the liquid fraction of said at least one liquid.

8. The method set forth in claim 5 wherein:

the fluid flowstream comprises a mixture of oil, water and a gas and the gas fraction is determined from the relationship:

$$fg = \frac{\sqrt{b^2 - 4ac}}{2a}$$

where fg is the gas fraction, wc is the fraction of water in the liquid phase, do is the density of oil in the liquid phase, dw is the density of water in the liquid phase, dg is the gas density, dma is the apparent density of the fluid mixture, a=dma*A3
b=dma*A2+wc(dw−do)+(do−dg)
c=dma−wc(dw−do)−do and A2 and A3 are empirical coefficients.

9. The method set forth in claim 5, wherein:

the Coriolis device comprises at least one tube through which the fluid flowstream is conveyed, said tube is vibrated in a lateral direction with respect to the direction of flow of fluid through said coriolis device and the density of the mixture (dm) is determined by the relationship:

$$dm = dma(1 + A2 \cdot fg + A3 \cdot fg^2)$$

wherein dma is the apparent density of the mixture as determined by the coriolis device, fg is, the gas fraction of the fluid mixture, and, A2 and A3 are empirical coefficients obtained by calibrating said densimeter with gassy liquid flow.

10. A method for determining the gas fraction of a fluid mixture comprising gas and at least two liquids in a liquid phase, comprising the steps of:

providing a flow meter characterized by a tube which is operable to be vibrated laterally with respect to the direction of flow of said fluid mixture through said tube, means for sensing the peak fluid pressure in said tube and the nominal fluid pressure in said tube, and means for measuring the frequency of vibration of said tube;

determining the density of the fluid mixture flowing through said tube;

vibrating said tube at a range of frequencies;

measuring the peak pressure in sad tube in relation to the vibration of said tube to determine when sad tube is vibrating at the sloshing natural frequency of vibration of said fluid mixture; and determining the gas fraction of the fluid mixture flowing through said tube based on the nominal pressure sensed by said pressure sensing means, said natural frequency of vibration of said fluid mixture, the density of said fluid mixture flowing through said tube, the bulk compressibility of the liquid in said fluid mixture and the diameter of said tube.

11. The method set forth in claim 10 wherein:

determining the sloshing natural frequency of vibration of said fluid mixture comprises comparing the phase angle of the waveform of said peak pressure with the phase angle of the waveform of said vibration of said tube.

12. The method set forth in claim 10 wherein:

the step of determining the density of said fluid mixture includes:

providing pressure sensing means disposed opposed to each other along a line which is parallel to the direction of vibration of said tube;

vibrating said tube at a frequency far from the sloshing natural frequency of vibration of the fluid mixture while measuring the pressure at the opposed pressure sensing means; and determining the density of the fluid mixture based on the pressure difference measured at the opposed pressure sensing means, the diameter of the tube, the amplitude of vibration of the tube and the frequency of vibration of the tube.

* * * * *